(12) United States Patent
Fritzler et al.

(10) Patent No.: US 12,315,693 B2
(45) Date of Patent: May 27, 2025

(54) EXTRA-FOCAL BEAM APERTURE DEVICE FOR AN X-RAY EMITTER

(71) Applicant: Siemens Healthineers AG, Forchheim (DE)

(72) Inventors: Anja Fritzler, Erlangen (DE); Petra Maurer, Heroldsbach (DE); Peter Geithner, Erlangen (DE); Christoph Jud, Nuremberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/882,864

(22) Filed: Sep. 12, 2024

(65) Prior Publication Data

US 2025/0095946 A1    Mar. 20, 2025

(30) Foreign Application Priority Data

Sep. 14, 2023  (DE) ...................... 10 2023 208 944.0

(51) Int. Cl.
*H01J 35/10* (2006.01)
*H01J 35/14* (2006.01)

(52) U.S. Cl.
CPC ............ *H01J 35/153* (2019.05); *H01J 35/10* (2013.01)

(58) Field of Classification Search
CPC ................................. H01J 35/10; H01J 35/153
See application file for complete search history.

(56) References Cited

U.S. PATENT DOCUMENTS

| | | |
|---|---|---|
| 4,803,711 A | 2/1989 | Tsujii et al. |
| 5,131,021 A | 7/1992 | Gard et al. |
| 2005/0265521 A1 | 12/2005 | Deuringer et al. |

(Continued)

FOREIGN PATENT DOCUMENTS

| | | |
|---|---|---|
| DE | 3632811 A1 | 4/1987 |
| DE | 102004052911 B4 | 4/2010 |

(Continued)

OTHER PUBLICATIONS

German Office Action and English translation thereof for German Application No. 102023208944.0 mailed Apr. 26, 2024.

(Continued)

*Primary Examiner* — Mark R Gaworecki
(74) *Attorney, Agent, or Firm* — Harness, Dickey & Pierce, P.L.C.

(57) ABSTRACT

One or more example embodiments relates to an extra-focal beam aperture device for an X-ray emitter and to the X-ray emitter. The extra-focal beam aperture device according to one or more example embodiments for an X-ray emitter has a planar beam-shaping element including an X-ray opaque material, the planar beam-shaping element being configured to form a useful X-ray beam and an X-ray measuring beam separate from the useful X-ray beam, from an X-ray beam bundle incident upon the extra-focal beam aperture device, the planar beam-shaping element including two side faces opposite each other, a radial lateral surface between the two side faces, a cross-section through the radial lateral surface having an approximately trapezoid shape, and at least one cut-out for shaping the X-ray measuring beam, the at least one cut-out having a tapering cross-section.

16 Claims, 6 Drawing Sheets

(56) References Cited

U.S. PATENT DOCUMENTS

2006/0093092 A1  5/2006  Kuhn
2022/0130568 A1  4/2022  Zambelli et al.

FOREIGN PATENT DOCUMENTS

| DE | 102004025119 B4 | 8/2012 | |
| EP | 3992619 A1 | 5/2022 | |
| WO | WO-2012123834 A1 * | 9/2012 | ............... G21K 1/02 |

OTHER PUBLICATIONS

German Decision to Grant and English translation thereof for German Application No. 102023208944.0 mailed Nov. 8, 2024.

* cited by examiner

EXTRA-FOCAL BEAM APERTURE DEVICE FOR AN X-RAY EMITTER

CROSS-REFERENCE TO RELATED APPLICATION(S)

The present application claims priority under 35 U.S.C. § 119 to German Patent Application No. 10 2023 208 944.0, filed Sep. 14, 2023, the entire contents of which is incorporated herein by reference.

FIELD

One or more example embodiments relates to an extra-focal beam aperture device for an X-ray emitter and to the X-ray emitter.

RELATED ART

A conventional X-ray tube has, in particular, an anode and a cathode that are arranged within an evacuated housing. An electric accelerating field is typically arranged between the anode and the cathode for accelerating electrons emitted at the cathode. Following the acceleration in the accelerating field, the electrons impact upon the anode in a focal spot in which an X-ray beam bundle can be generated by an interaction of the incident electrons with the anode.

The accelerating field is provided, in particular, by an acceleration unit. The acceleration unit is, in particular, an accelerating voltage source or a high frequency source.

Depending upon the X-ray tube, the accelerating field can be configured relatively simple, in particular if the spacing between the anode and the cathode is relatively small. In this case, the accelerating field can generated and switched off substantially by way of a switching on and off of the acceleration unit. The more complex the X-ray tube is, the more feature-rich the acceleration unit typically is.

For example, the acceleration unit can comprise a deflecting unit and/or a focusing unit. The focusing unit can be configured, in particular, to influence the accelerating field such that a dimension of the focal spot, that is, its diameter, length and/or width on the anode can be changed. The deflecting unit is configured, in particular, to influence the accelerating field such that a position of the focal spot on the anode can be changed. In the case of a rotating anode X-ray tube, a deflection region in which the position of the focal spot is changeable is typically substantially smaller than in a rotating envelope X-ray tube. The reason for this is that with a rotating anode X-ray tube, the cathode is typically arranged decentrally in relation to the rotation axis of the anode directly over the focal spot and/or over a focal path formed by the focal spots annularly displaced by way of the rotation of the anode. By contrast, in the rotating envelope X-ray tube, the cathode is arranged on the rotation axis centrally over the anode, so that the electrons emitted there have to be deflected over a longer path to the decentralized focal path as compared with the rotating anode X-ray tube.

In order that a regulation of the position of the focal spot is possible, in particular, a focal spot predicting unit and/or an X-ray beam measuring device can be used. The X-ray beam measuring device is oriented, in particular, toward the focal spot of the anode in order preferably to be able to detect the focal spot directly, in effect to view it. So that the X-ray beam measuring device can detect the focal spot, typically a cross-section of the X-ray beam bundle of the anode of an X-ray tube of this type is relatively large.

The larger a cross-section of the X-ray beam bundle is, the more X-rays generated in the focal spot fall upon an X-ray detector. Ideally, only the useful X-ray beam, which typically comprises exclusively X-rays generated in the focal spot and/or is free from scattered rays, falls upon the X-ray detector. The useful X-ray beam comprises, in particular, an imaging part of the X-ray beam bundle. In particular, X-rays which arise outside the focal spot by way of electrons that are incident in a random manner upon the anode and form the so-called extra-focal beam, often negatively influence an image quality of the images reconstructed via the X-rays captured on the X-ray detector. A reduction of the cross-section of the X-ray beam bundle that is carried out by way of a conventional frame-like collimator, through the cut-out of which the X-ray beam bundle passes is often not or is only partially possible since the visibility of the focal spot to the X-ray beam measuring device must still be ensured.

SUMMARY

One or more example embodiments provides an extra-focal beam aperture device for an X-ray emitter and the X-ray emitter in which the proportion of scattered radiation in the X-ray beam bundle can be reduced.

Independent of the grammatical term usage, individuals with male, female or other gender identities are included within the term.

BRIEF DESCRIPTION OF THE DRAWINGS

One or more example embodiments will now be described and explained in greater detail making reference to the illustrated drawings. In principle, structures and units which remain essentially the same are identified in the following description of the figures with the same reference signs as on the first occurrence of the relevant structure or unit.

In the drawings.

DETAILED DESCRIPTION

Figure 1:
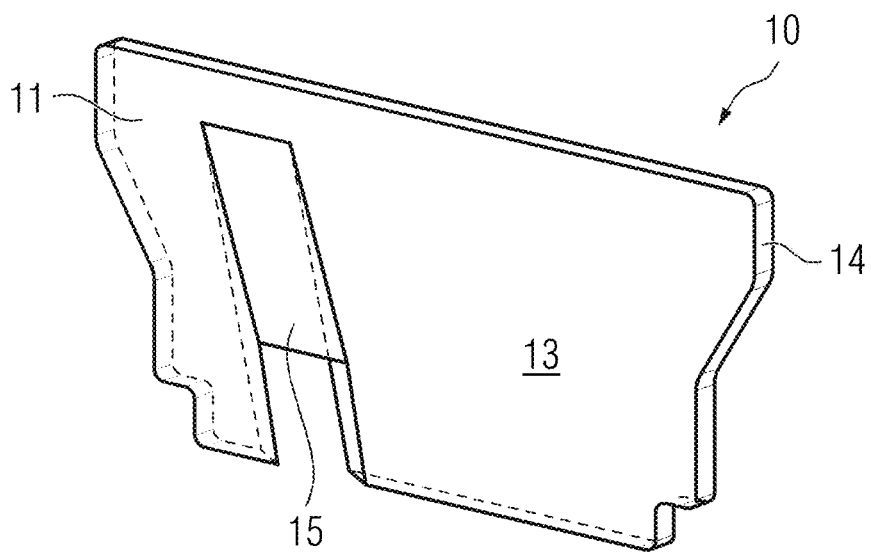
FIG. 1 shows an extra-focal beam aperture device according to one or more example embodiments.

The extra-focal beam aperture device according to one or more example embodiments for an X-ray emitter has a planar beam-shaping element made of an X-ray opaque material, wherein the planar beam-shaping element is configured to form a useful X-ray beam and additionally, separately therefrom, an X-ray measuring beam, from an X-ray beam bundle incident upon the extra-focal beam aperture device, wherein the planar beam-shaping element has two side faces arranged opposite one another and, between them, a radial lateral surface, wherein a cross-section through the radial lateral surface has an approximately trapezoid shape, wherein the planar beam-shaping element has at least one cut-out for shaping the X-ray measuring beam, wherein the at least one cut-out has a tapering cross-section.

The X-ray emitter according to one or more example embodiments has an X-ray tube for generating an X-ray beam bundle and
the extra-focal beam aperture device according to one or more example embodiments, wherein the X-ray tube has an X-ray beam outlet window for the X-ray beam bundle, wherein the extra-focal beam aperture device is arranged perpendicularly to the X-ray beam outlet window such that the side faces of the planar beam-shaping element are oriented approximately parallel to the X-ray beam bundle.

An advantage of the extra-focal beam aperture device according to one or more example embodiments is that by way of the separation of the useful X-ray beam from the X-ray measuring beam, the X-ray beam bundle can be subdivided. The subdivision of the X-ray beam bundle is advantageous, in particular, since thereby an image quality can be enhanced. Overall, scattered radiation negatively affecting the image quality can be reduced. Particularly advantageous is a reduction in the extra-focal beam by way of the extra-focal beam aperture device according to one or more example embodiments.

The planar beam-shaping element is configured thin, in particular, in the thickness direction of the beam-shaping element. It can be advantageous to configure the beam-shaping element as thin as possible. In particular, a dimension in the thickness direction of the beam-shaping element is greater, in particular, by at least a factor of 2, preferably by a factor of 5 or by a factor of greater than 10, than a dimension in one of the two directions perpendicular to the thickness direction. The dimensions perpendicular to the thickness direction can be the same or can differ and are, in particular, longitudinal directions. The dimensions in the respective spatial direction can be constant or can vary, at least partially.

The planar beam-shaping element consists of the X-ray opaque material. The X-ray opaque material can be configured, in particular, for a separation of the useful X-ray beam and the X-ray measuring beam in that the X-ray beam bundle is partially attenuated by the X-ray opaque material in one region and this region separates the useful X-ray beam from the X-ray measuring beam.

The shaping of the useful X-ray beam and of the X-ray measuring beam comprises, in particular, the subdivision of the X-ray beam bundle into two separate parts, in particular the useful X-ray beam and the X-ray measuring beam. The shaping of the useful X-ray beam and of the X-ray measuring beam comprises, in particular, a subdivision of this type of the X-ray beam bundle, such that the useful X-ray beam is detectable via an X-ray detector and that the X-ray measuring beam is detectable via an X-ray beam measuring device.

The fact that the X-ray measuring beam is also formed in addition to, and separate from, the useful X-ray beam means, in particular, that the useful X-ray beam is a first partial X-ray beam bundle and the X-ray measuring beam is a second partial X-ray beam bundle, wherein the first partial X-ray beam bundle and the second partial X-ray beam bundle are detectable and/or able to be captured independently of one another.

During the shaping of the X-ray beam bundle, in particular, no X-ray radiation is added. The shaping of the useful X-ray beam and of the X-ray measuring beam comprises, in particular, an attenuation of part of the X-rays of the X-ray beam bundle.

The shaping of the useful X-ray beam and/or of the X-ray measuring beam comprises, in particular, no stopping down of the useful X-ray beam and/or of the X-ray measuring beam. The stopping down of X-rays typically corresponds to a total absorption.

The subdivision of the X-ray beam bundle by way of the planar beam-shaping element can take place one-to-one. Alternatively, it is conceivable that, in particular, the useful X-ray beam comprises more X-rays of the X-ray beam bundle than the X-ray measuring beam.

The X-ray opaque material can have, in particular, a metal. The metal can be, in particular, brass, tungsten, lead and/or molybdenum. The X-ray opaque material can additionally have, in particular, in addition to the metal, a plastics material. The X-ray opaque material can be, in particular, an additively produced material and/or a solid material.

The X-ray beam bundle relates, in particular, to the radially lateral surface of the planar beam-shaping element. The radial lateral surface has a constant dimension, in particular, in the thickness direction, so that the beam-shaping element has a substantially constant thickness subject to the cut-outs. Alternatively, it is conceivable that the radial lateral surface has an increasing dimension in the thickness direction, so that the planar beam-shaping element has, for example, a wedge shape with an angle of less than 10°. The angle can depend, in particular, upon a spacing of the extra-focal beam aperture device from the focal spot generating the X-ray beam bundle.

The side faces of the planar beam-shaping element extend, in particular, in the longitudinal direction of the planar beam-shaping element. In particular, given a constant thickness of the beam-shaping element, the side faces are aligned parallel to one another. Alternatively, given a wedge shape of the planar beam-shaping element, the side faces are aligned angled toward one another, in particular, at the angle of the wedge shape. The two side faces situated opposite one another and the radial lateral surface lying therebetween delimit, in particular, the volume of the planar beam-shaping element.

The fact that the cross-section through the radial lateral surface has approximately the trapezoid form means, in particular, that the dimension in one of the longitudinal directions of the beam-shaping element increases or decreases, while the dimension in the other of the longitudinal directions of the beam-shaping element, in particular, is constant. The "approximately" relates, in particular, to the corner points of the beam-shaping element in the two longitudinal directions. Approximately means, in particular, that the increase or decrease can occur in portions and/or can be omitted in portions. The cross-section through the radial lateral surface is, in particular, perpendicular to the thickness direction of the beam-shaping element.

The increase or decrease can be interrupted, in particular, by a lateral deviation in the beam-shaping element. The lateral deviation in the beam-shaping element differs from the at least one cut-out, in particular, in its position and/or in its function. The lateral deviation is provided, in particular, for a fastening of the extra-focal beam aperture device. The lateral deviation is, in particular, not exposed to X-rays of the X-ray beam bundle. In contrast to the lateral deviation, the at least one cut-out is exposed to the X-ray beam bundle and/or has no influence on the increase or decrease in the dimension in one of the two longitudinal directions of the beam-shaping element. The lateral deviation is, in particular, step-shaped.

The at least one cut-out typically interrupts the volume of the planar beam-shaping element. The volume of the planar beam-shaping element is reduced, in particular, by the at least one cut-out. The at least one cut-out forms, in particular, a hollow space within an envelope which is defined by the two mutually opposed side faces and the radial lateral surface. The volume of the at least one cut-out is enclosed, in particular, by the at least one cut-out and the envelope.

In addition to a portion with the tapering cross-section, the at least one cut-out can have a further portion with a constant cross-section. The tapering of the cross-section typically takes place parallel to the propagation direction of the X-ray beam bundle. The tapering of the cross-section of the at least one cut-out can take place with or against the direction in which the trapezoid form of the cross-section through the lateral surface tapers.

The tapering cross-section of the at least one cut-out relates, in particular, to the hollow space within the envelope. The hollow space can have, in particular, a wedge-shaped portion. In addition, the hollow space can have a cuboid portion.

The cross-section of the at least one cut-out can have an angular or round shape. The cross-section can, in particular, have a rectangular shape or a trapezoid shape or a parallelogram shape.

The at least one cut-out adjoins, in particular, a boundary area of the planar beam-shaping element. The at least one cut-out can be configured such that the boundary area of the planar beam-shaping element is rectangular or trapezoid.

The shaping of the X-ray measuring beam via the at least one cut-out takes place, in particular, in addition to the shaping via the planar beam-shaping element. Approximately speaking, the shaping via the planar beam-shaping element can be regarded as the subdivision of the X-ray beam bundle into the useful X-ray beam and the X-ray measuring beam, as well as the forming, via the at least one cut-out, of a further restriction of the X-ray measuring beam. The shaping of the X-ray measuring beam via the at least one cut-out can comprise a partial attenuation of the X-ray measuring beam. The at least one cut-out shapes the X-ray measuring beam, in particular, by way of a delimitation of the X-ray measuring beam.

One embodiment provides that the at least one cut-out divides the planar beam-shaping element into two separate parts. The two separate parts are not directly connected, in particular physically, to one another. In this embodiment, the beam-shaping element is configured, in particular, in two parts.

If the at least one cut-out does not divide the planar beam-shaping element into at least two separate parts, the planar beam-shaping element is formed, in particular, in one piece. In this case, a stability of the planar beam-shaping element can advantageously be increased.

One embodiment provides that the planar beam-shaping element is configured in one piece as a portion of a block of the same X-ray opaque material,
wherein the block has a tapering external form, wherein the radial lateral surface of the planar beam-shaping element is part of the external form of the block,
wherein the block surrounds a tapering through shaft for the useful X-ray beam,
wherein the through shaft for the useful X-ray beam and the at least one cut-out of the planar beam-shaping element for shaping the X-ray measuring beam via the planar beam-shaping element are separated, and
wherein the volume enclosed by the through shaft is larger by a factor of at least 2 than the volume enclosed by the at least one cut-out.

This embodiment is, in particular, advantageous since it enables a better adaptation of the extra-focal beam aperture device to the X-ray emitter. In particular, the block of the extra-focal beam aperture device can be adapted to the X-ray emitter precisely-fitting. Furthermore, the shaft walls of the through shaft enable a more precise definition of the useful X-ray beam.

The extra-focal beam aperture device has, in particular, the block. The block has, in particular, the planar beam-shaping element. In addition to the planar beam-shaping element, the block typically has a further portion. In particular, the further portion and the planar beam-shaping element delimit the through shaft. The block, that is in particular, the planar beam-shaping element and the further portion of the block is, in particular, configured in one piece and/or from the same X-ray opaque material. The planar beam-shaping element and the further portion are, for example, configured via an additive manufacturing method in one piece. An alternative method for configuring the block in one piece is primary shaping or reshaping.

The radial lateral surface of the planar beam-shaping element forms, in particular, part of the external form of the block. The trapezoid form of the cross-section through the radial lateral surface of the planar beam-shaping element is, in particular, part of the external form of the block. The trapezoid form of the cross-section through the radial lateral surface of the planar beam-shaping element is preferably substantially congruent with the tapering external form of the block. In other words, the trapezoid form of the cross-section through the radial lateral surface of the planar beam-shaping element preferably defines the increase or decrease of the tapering external form.

The tapering through shaft has, in particular, a tapering cross-section. The tapering through shaft is, in particular, completely embedded in the block. The tapering through shaft has substantially a straight extent. The block has, in particular, two mutually opposing openings for the through shaft which are arranged along a spatial direction, in particular one of the two longitudinal directions. The openings can have, in particular, a round or angular form. The openings can be configured, in particular, slit-like.

The separation of the through shaft and the at least one cut-out via the planar beam-shaping element means, in particular, that the through shaft and the at least one cut-out are arranged on opposite sides of the beam-shaping element. The planar beam-shaping element is arranged, in particular, between the at least one cut-out and the through shaft.

If the at least one cut-out divides the planar beam-shaping element into two separate parts, the block is configured, in particular, C-shaped. In this case, the end faces of the C-shaped block are preferably oriented toward one another in the direction of the through shaft, so that in a particular configuration, the beam-shaping element separates the through shaft from the at least one cut-out. In this case, a cross-section of the at least one cut-out is configured, in particular, in the form of a trapezoid or parallelogram.

The volume enclosed by the through shaft is, in particular, the volume of the through shaft. The volume of the through shaft is enclosed, in particular, by the shaft walls of the through shaft and the openings of the through shaft. The volume enclosed by the at least one cut-out is, in particular, the volume of the at least one cut-out, preferably the volume of the hollow space formed by the at least one cut-out. The volume of the through shaft can be multiple times larger than the volume of the at least one cut-out. The factor can be, in particular, 5, 10 or 50.

One embodiment provides that the exterior form of the block is a truncated pyramidal form. In the truncated pyramidal form, a cross-section of the block perpendicular to the longitudinal extent of the through shaft is substantially angular, for example, rectangular. Alternatively, the exterior form of the block can be a truncated conical form. In the truncated conical form, the cross-section of the block perpendicular to the longitudinal extent of the through shaft is substantially round.

One embodiment provides that the block has a cut-out for a holder for an X-ray beam measuring device. Advantageously, the planar beam-shaping element is arranged between this cut-out and the through shaft. In other words, the cut-out for the holder for the X-ray beam measuring device and the through shaft are arranged on opposite sides of the planar beam-shaping element. The cut-out for the holder for the X-ray beam measuring device is, in particular, cylindrical. The planar beam-shaping element can form a lateral surface of the cut-out for the holder for the X-ray beam measuring device in the peripheral direction by at least 22.5°, preferably at least 90° or 360°. In the latter case, the cut-out for the holder for the X-ray beam measuring device is completely embedded in the planar beam-shaping element and is, so to speak, closed. Otherwise, where smaller than 360°, the cut-out for the holder for the X-ray beam measuring device is open. The cut-out for the holder for the X-ray beam measuring device can consist of a plurality of cylindrical portions, wherein the diameter of at least two of the cylindrical portions differs.

One embodiment provides that the block has a further tapering through shaft for the X-ray measuring beam, wherein the further through shaft is delimited by the at least one cut-out of the planar beam-shaping element. The further through shaft is embedded, in particular, completely in the block. The at least one cut-out forms at least one shaft wall of the further through shaft. The further through shaft has a substantially straight extent. The block has, in particular, two further mutually opposing openings for the further through shaft which are arranged along a spatial direction, in particular one of the two longitudinal directions. The further openings can have, in particular, a round or angular form. The further openings can, in particular, be configured slit-like. The tapering through shaft has, in particular, a tapering cross-section.

It is fundamentally conceivable that the tapering direction of the through shaft differs from the tapering direction of the further through shaft, in particular, that it is substantially antiparallel. Alternatively, the tapering direction of the through shaft can match the tapering direction of the further through shaft, in particular, it can be substantially parallel.

One embodiment provides that, in addition to the planar beam-shaping element, the block has a part configured at least as a shell and in that the part configured as a shell and the planar beam-shaping element delimit the further through shaft. In this embodiment, the extra-focal beam aperture device is configured in at least two parts. The part configured as a shell can have, in particular, an elevation which reduces the volume enclosed by the at least one cut-out, but typically does not completely fill it. The elevation and the at least one cut-out can be configured, in particular, complementary.

The X-ray tube has, in particular, an anode and a cathode that are arranged within an evacuated housing. An electric accelerating field is typically arranged between the anode and the cathode for accelerating electrons emitted at the cathode. Following the acceleration in the accelerating field, the electrons impact upon the anode preferably in a focal spot in which an X-ray beam bundle can be generated by an interaction of the incident electrons with the anode. The accelerating field is provided, in particular, by an acceleration unit. The acceleration unit is, in particular, an accelerating voltage source or a high frequency source. The electron emitter can be, in particular, a thermionic emitter or a field effect emitter.

The X-ray beam outlet window is typically a part of the evacuated housing. It is conceivable that a delimited region of the evacuated housing forms the X-ray beam outlet window, in particular if the housing consists of an X-ray transparent material, for example, glass. Alternatively, an X-ray transparent component can be integrated into the evacuated housing as the X-ray beam outlet window.

The extra-focal beam aperture device is preferably arranged perpendicularly on the, or to the, X-ray beam outlet window. The extra-focal beam aperture device is fixedly connected, in particular, to the X-ray tube. Typically, the arrangement of the extra-focal beam aperture device is rigid relative to the X-ray tube. In this case, in particular, the extra-focal beam aperture device is immovable relative to the X-ray beam bundle. It follows therefrom more typically that the proportional subdivision of the X-ray beam bundle into the useful X-ray beam and the X-ray measuring beam is unchangeable.

One embodiment provides that the X-ray tube is mounted able to rotate relative to the extra-focal beam aperture device. In this case, in particular, the evacuated housing of the X-ray tube is mounted able to rotate relative to the extra-focal beam aperture device. If the X-ray tube, in particular, the evacuated housing is mounted able to rotate relative to the extra-focal beam aperture device, the X-ray tube is, in particular, a rotating envelope X-ray tube.

In an alternative embodiment, the evacuated housing can be configured non-rotatably relative to the extra-focal beam aperture device. In this case, in particular, the anode is mounted able to rotate relative to the extra-focal beam aperture device and the X-ray tube is typically a rotating anode X-ray tube.

One embodiment provides that the X-ray emitter further has a collimator, wherein the extra-focal beam aperture device is oriented between the X-ray tube and the collimator, wherein the collimator is oriented for collimation of the useful X-ray beam. The collimation of the useful X-ray beam does not influence, in particular, the X-ray measuring beam. The collimator can comprise, in particular, immovable and/or dynamic, that is movable, collimator apertures.

FIG. 1 shows an extra-focal beam aperture device 10 according to one or more example embodiments from a first perspective.

The extra-focal beam aperture device 10 for an X-ray emitter 20, not shown in FIG. 1, has a planar beam-shaping element 11 made of an X-ray opaque material. The planar beam-shaping element 11 is configured to form a useful X-ray beam and additionally, separately therefrom, an X-ray measuring beam, from an X-ray beam bundle incident upon the extra-focal beam aperture device. The planar beam-shaping element 11 has two side faces 12, 13 arranged opposite one another and, between them, a radial lateral surface 14. A cross-section through the radial lateral surface 14 has an approximately trapezoid shape. The planar beam-shaping element 11 has at least one cut-out 15 for shaping the X-ray measuring beam. The at least one cut-out 15 has a tapering cross-section.

The X-ray opaque material can have a metal, in particular, brass, tungsten, lead and/or molybdenum. Alternatively or additionally, the X-ray opaque material can have a plastics material. The X-ray opaque material can be an additively produced material. Alternatively or additionally, the X-ray opaque material can be a solid material.

Figure 2:
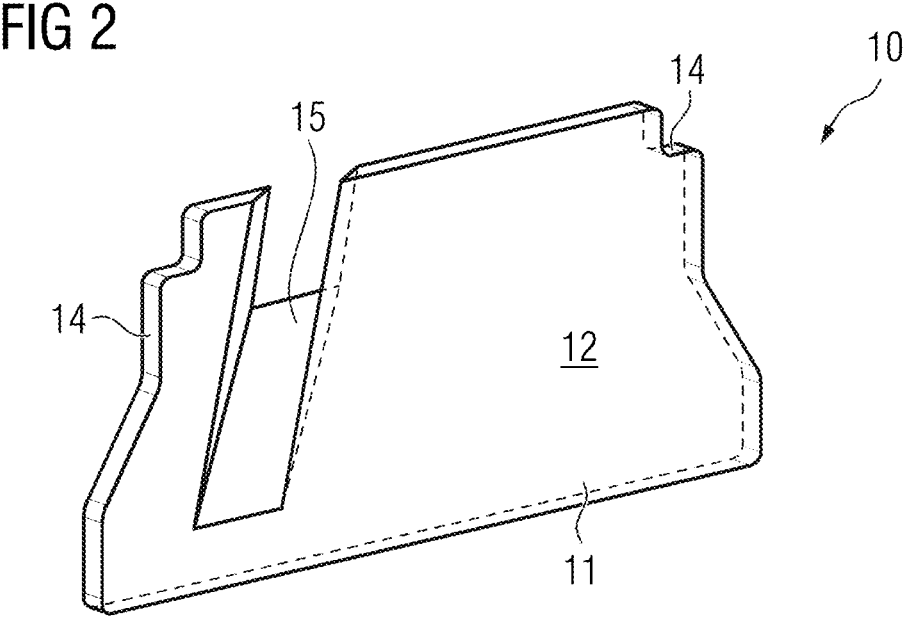
FIG. 2 shows the extra-focal beam aperture device according to one or more example embodiments.

FIG. 2 shows the extra-focal beam aperture device 10 of FIG. 1 from a second perspective different from the first.

Figure 3:
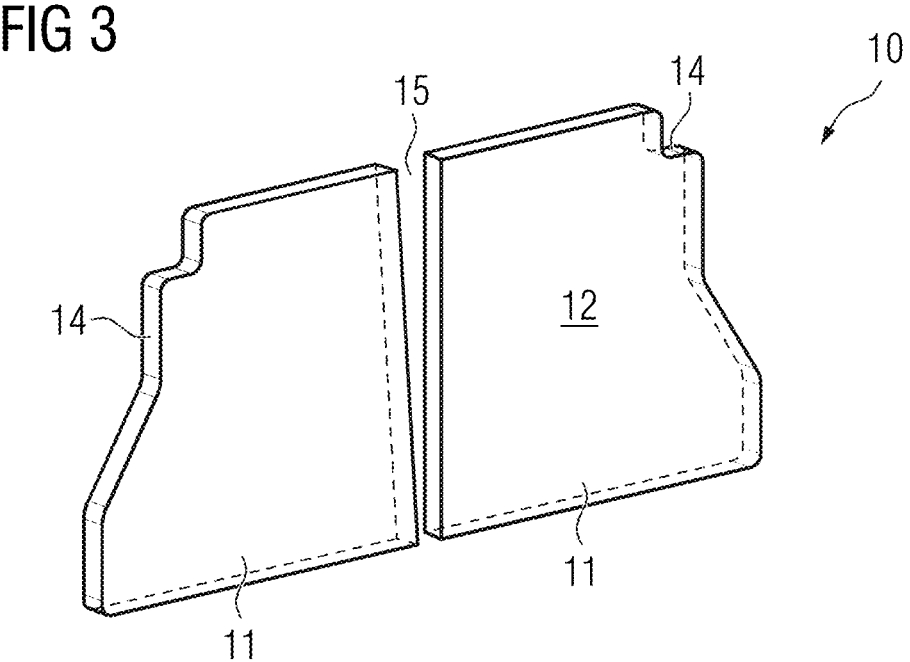
FIG. 3 shows a first exemplary embodiment of the extra-focal beam aperture device.

FIG. 3 shows a first exemplary embodiment of the extra-focal beam aperture device 10.

The configuration of the at least one cut-out 15 in FIG. 3 differs from the embodiment of the at least one cut-out 15 in FIGS. 1 and 2. The at least one cut-out 15 separates the planar beam-shaping element 11 into two separate parts.

Figure 4:
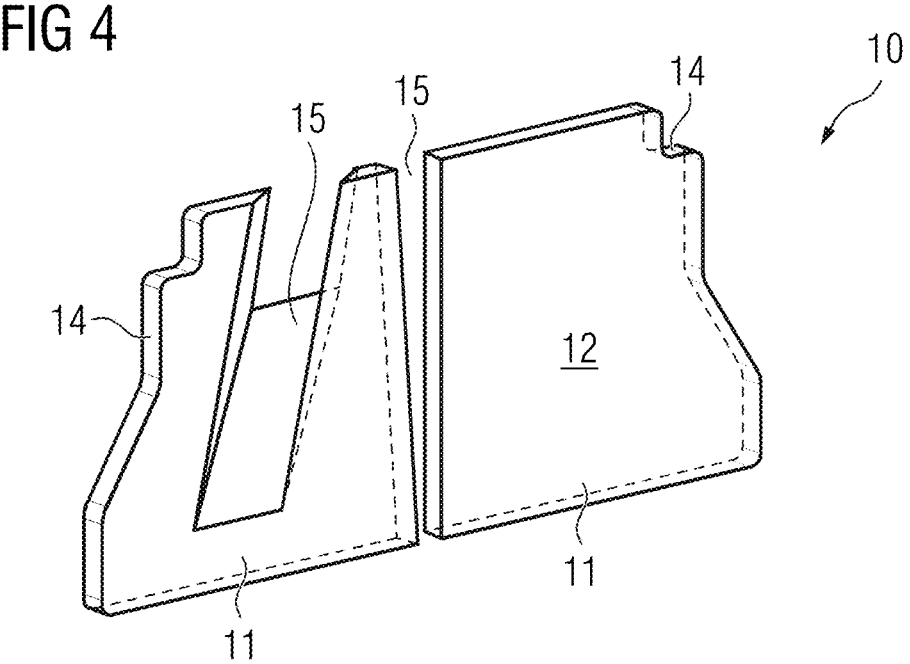
FIG. 4 shows a second exemplary embodiment of the extra-focal beam aperture device.

FIG. 4 shows a second exemplary embodiment of the extra-focal beam aperture device 10.

The planar beam-shaping element 11 of FIG. 4 has a first cut-out 15 for forming a first X-ray measuring beam and a second cut-out 15 for forming a second X-ray measuring beam. The exemplary embodiment of FIG. 4 substantially combines the configurations of the at least one cut-out 15 in FIGS. 2 and 3.

Figure 5:
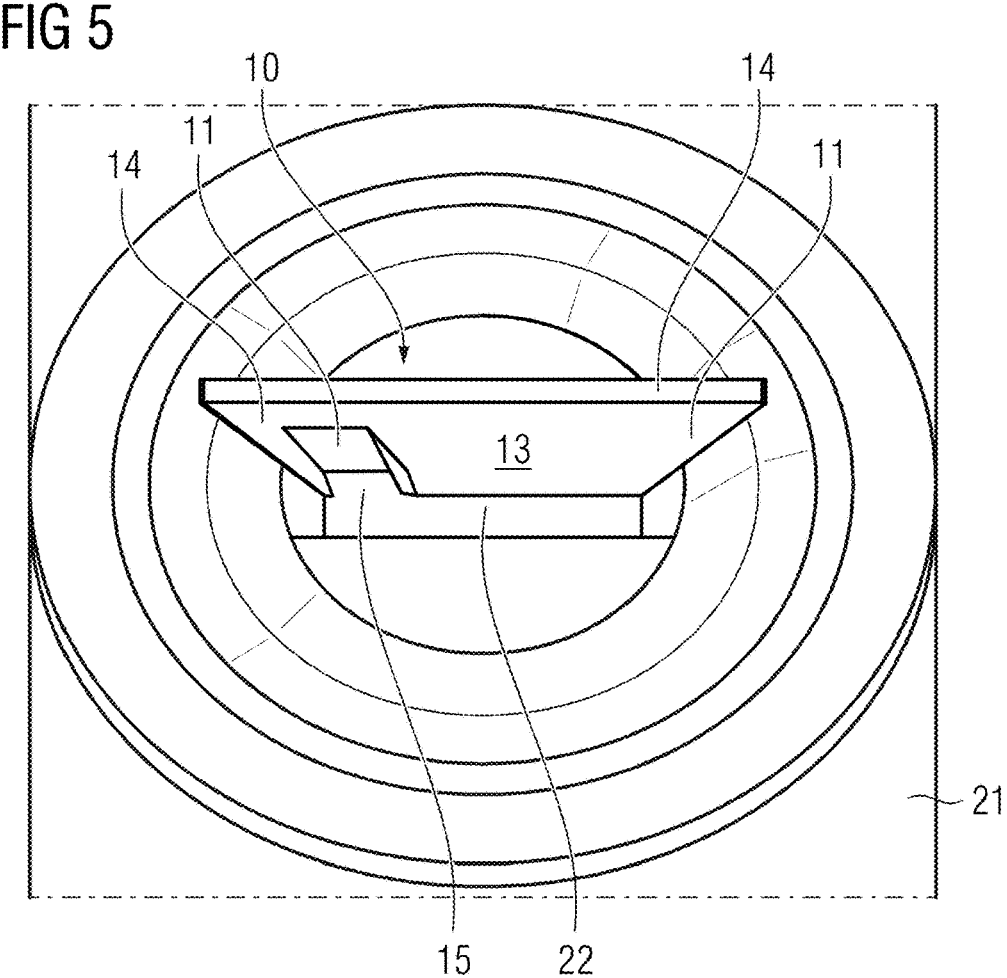
FIG. 5 shows an X-ray emitter according to one or more example embodiments.

FIG. 5 shows portions of an X-ray emitter 20 according to one or more example embodiments in a perspective view.

The X-ray emitter 20 has an X-ray tube 21 for generating an X-ray beam bundle and an extra-focal beam aperture device 10. The X-ray tube 21 has an X-ray beam outlet window 22 for the X-ray beam bundle. The extra-focal beam aperture device 10 is arranged perpendicularly to the X-ray beam outlet window 22 such that the side faces 12, 13 of the planar beam-shaping element 11 are oriented approximately parallel to the X-ray beam bundle. In this exemplary embodiment, the X-ray emitter 20 has a truncated conical receptacle.

Figure 6:
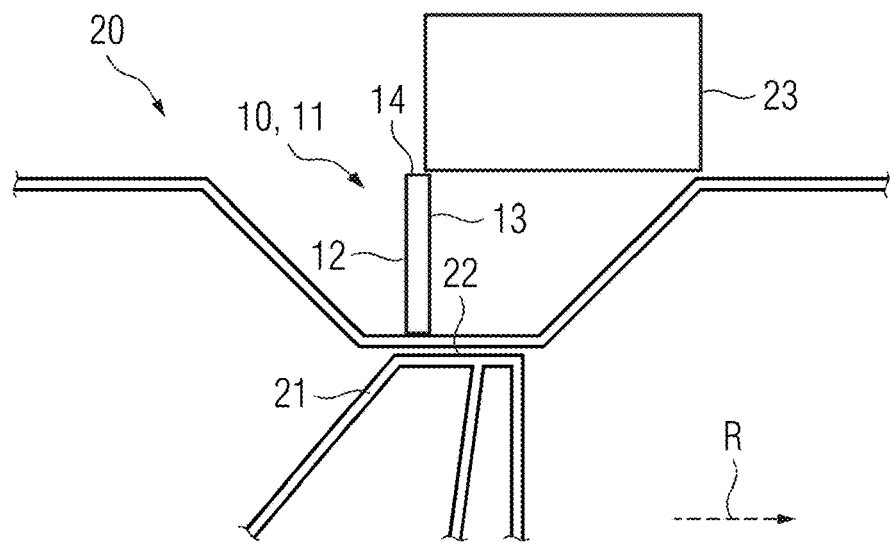
FIG. 6 shows a first exemplary embodiment of the X-ray emitter.

FIG. 6 shows a first exemplary embodiment of the X-ray emitter 20 in a longitudinal section.

The X-ray emitter further has a collimator 23. The extra-focal beam aperture device is arranged between the X-ray tube 21 and the collimator 23. The collimator 23 is configured for collimating the useful X-ray beam. In this exemplary embodiment, the X-ray tube 21 is configured as a rotating envelope X-ray tube, in that the X-ray tube 21 is mounted able to be rotated relative to the extra-focal beam aperture device 10.

Figure 7:
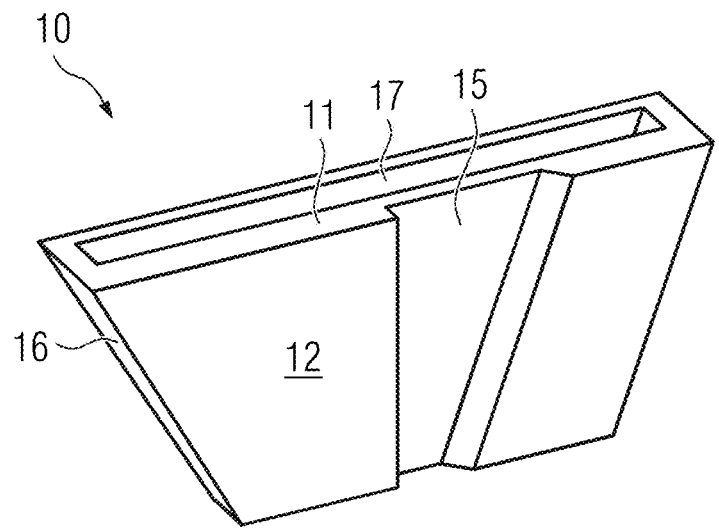
FIG. 7 shows a third exemplary embodiment of the extra-focal beam aperture device.

FIG. 7 shows a third exemplary embodiment of the extra-focal beam aperture device 10.

The planar beam-shaping element 11 is configured in one piece as a portion of a block 16 of the same X-ray opaque material. The block 16 has a tapering external form. The radial lateral surface of the planar beam-shaping element is part of the external form of the block. The block 16 surrounds a tapering through shaft 17 for the useful X-ray beam. The through shaft 17 for the useful X-ray beam and the at least one cut-out 15 of the planar beam-shaping element 11 for shaping the X-ray measuring beam are separated via the planar beam-shaping element 11. The volume enclosed by the through shaft 17 is larger by a factor of at least 2 than the volume enclosed by the at least one cut-out 15.

In this exemplary embodiment, the exterior form of the block 16 is a truncated pyramidal form. In an alternative exemplary embodiment, it is conceivable that the exterior form of the block 16 is a truncated conical form.

Figure 8:
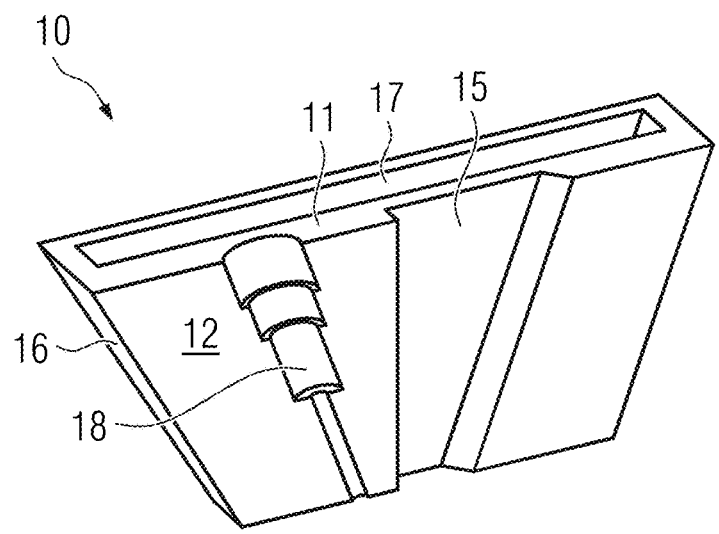
FIG. 8 shows a fourth exemplary embodiment of the extra-focal beam aperture device.

FIG. 8 shows a fourth exemplary embodiment of the extra-focal beam aperture device 10. The block 16 has a cut-out 18 for a holder for an X-ray beam measuring device.

Figure 9:
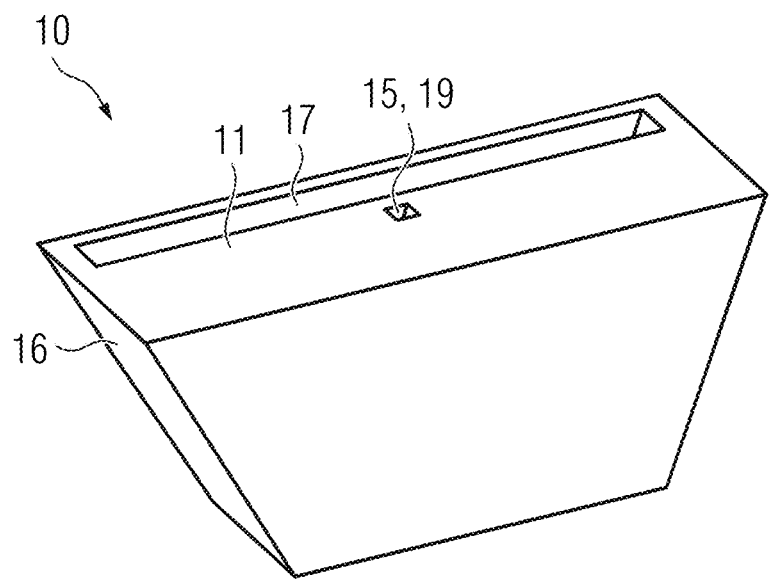
FIG. 9 shows a fifth exemplary embodiment of the extra-focal beam aperture device.

FIG. 9 shows a fifth exemplary embodiment of the extra-focal beam aperture device 10.

The block 16 surrounds a further tapering through shaft 19 for the useful X-ray measuring beam. The further through shaft 19 is delimited by the at least one cut-out 15 of the planar beam-shaping element 11.

Figure 10:
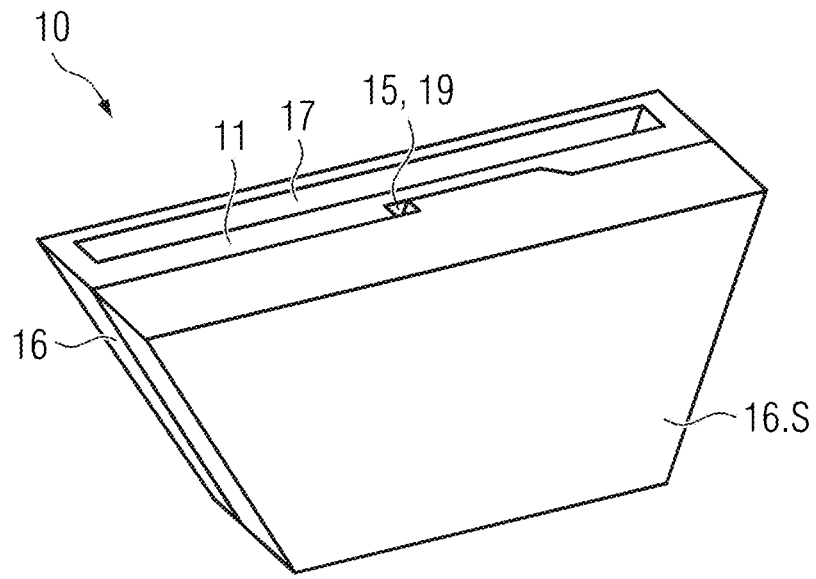
FIG. 10 shows a sixth exemplary embodiment of the extra-focal beam aperture device.

FIG. 10 shows a sixth exemplary embodiment of the extra-focal beam aperture device 10 as an alternative to the fifth exemplary embodiment.

In addition to the planar beam-shaping element 11, the block 16 also has at least one part 16. S configured as a shell. The part 16.S configured as a shell and the planar beam-shaping element 11 delimit the further through shaft 19.

Figure 11:
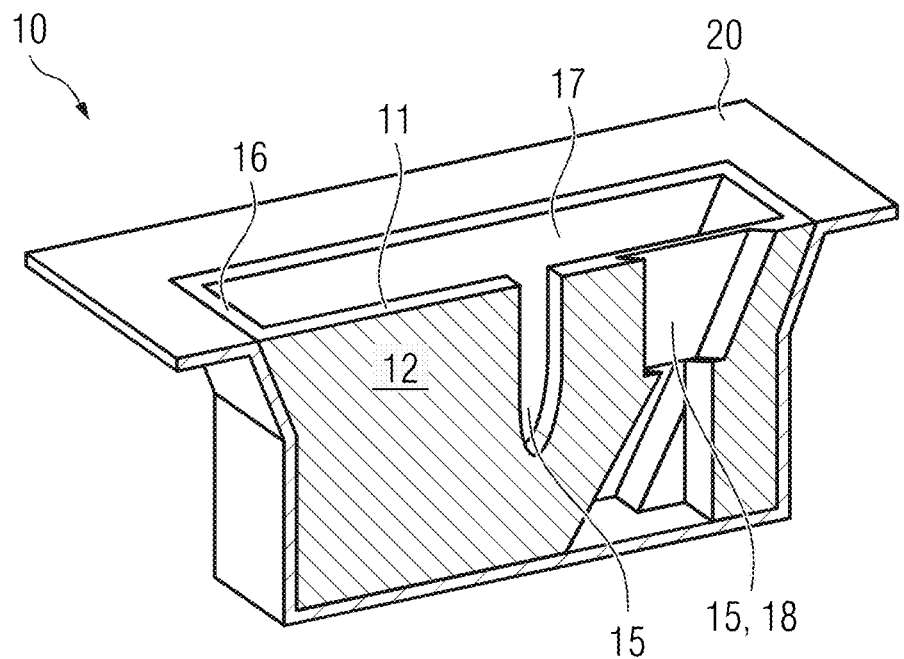
FIG. 11 shows a seventh exemplary embodiment of the extra-focal beam aperture device.

FIG. 11 shows a seventh exemplary embodiment of the extra-focal beam aperture device 10 in a cross-sectional view.

The planar beam-shaping element 11 has two cut-outs 15. The block 16 has a truncated pyramidal form and is adapted in exactly fitting manner to the X-ray emitter 20, only a portion of which is shown. For the exactly fitting arrangement of the extra-focal beam aperture device 10, in this exemplary embodiment, the X-ray emitter 20 has a truncated pyramidal receptacle. In this receptacle, the extra-focal beam aperture device 10 can be fastened via a fastening means, in particular releasably. The fastening means can comprise, in particular, a plug-in connection, a screw-fastening means (e.g., screw fastener) and/or an adhesive means (e.g., an adhesive).

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments. The present invention may, however, be embodied in many alternate forms and should not be construed as limited to only the embodiments set forth herein.

Although the invention has been illustrated and described in detail by way of the preferred exemplary embodiments, the invention is nevertheless not restricted by the examples given and other variations can be derived therefrom by a person skilled in the art without departing from the protective scope of the invention.

The invention claimed is:

1. An extra-focal beam aperture device for an X-ray radiator, the aperture device comprising:
   a planar beam-shaping element including an X-ray opaque material, the planar beam-shaping element being configured to form a useful X-ray beam and an X-ray measuring beam separate from the useful X-ray beam, from an X-ray beam bundle incident upon the extra-focal beam aperture device, the planar beam-shaping element including,
   two side faces opposite each other,
   a radial lateral surface between the two side faces, a cross-section through the radial lateral surface having an approximately trapezoid shape, and
   at least one cut-out for shaping the X-ray measuring beam, the at least one cut-out having a tapering cross-section.

2. The extra-focal beam aperture device of claim 1, wherein the at least one cut-out separates the planar beam-shaping element into two separate parts.

3. The extra-focal beam aperture device of claim 2, wherein
   the planar beam-shaping element is configured in one piece as a portion of a block of the same X-ray opaque material,
   the block has a tapering external form, the radial lateral surface of the planar beam-shaping element is part of an external form of the block,
   the block surrounds a tapering through shaft for the useful X-ray beam,
   the tapering through shaft for the useful X-ray beam and the at least one cut-out of the planar beam-shaping element for shaping the X-ray measuring beam are separated via the planar beam-shaping element, and
   a volume enclosed by the through shaft is larger by a factor of at least 2 than a volume enclosed by the at least one cut-out.

4. The extra-focal beam aperture device of claim 1, wherein the X-ray opaque material includes a metal.

5. The extra-focal beam aperture device of claim 4, wherein the X-ray opaque material includes at least one of brass, tungsten, lead or molybdenum.

6. The extra-focal beam aperture device of claim 1, wherein the X-ray opaque material includes a plastics material.

7. The extra-focal beam aperture device of claim 1, wherein the X-ray opaque material is an additively manufactured material.

8. The extra-focal beam aperture device of claim 1, wherein the X-ray opaque material is a solid material.

9. The extra-focal beam aperture device of claim 1, wherein
   the planar beam-shaping element is configured in one piece as a portion of a block of the same X-ray opaque material,
   the block has a tapering external form, the radial lateral surface of the planar beam-shaping element is part of an external form of the block,
   the block surrounds a tapering through shaft for the useful X-ray beam,
   the tapering through shaft for the useful X-ray beam and the at least one cut-out of the planar beam-shaping element for shaping the X-ray measuring beam are separated via the planar beam-shaping element, and
   a volume enclosed by the through shaft is larger by a factor of at least 2 than a volume enclosed by the at least one cut-out.

10. The extra-focal beam aperture device of claim 9, wherein an exterior form of the block is a truncated pyramidal form.

11. The extra-focal beam aperture device of claim 9, wherein the block has a cut-out for a holder for an X-ray beam measuring device.

12. The extra-focal beam aperture device of claim 9, wherein
- the block has a further tapering through shaft for the X-ray measuring beam, and
- the further tapering through shaft is delimited by the at least one cut-out of the planar beam-shaping element.

13. The extra-focal beam aperture device of claim 12, wherein
- the block has at least one part configured as a shell, and
- the part configured as the shell and the planar beam-shaping element delimit the further tapering through shaft.

14. An X-ray emitter, comprising:
- an X-ray tube configured to generate an X-ray beam bundle; and
- the extra-focal beam aperture device of claim 1,
- wherein the X-ray tube has an X-ray beam outlet window for the X-ray beam bundle and the extra-focal beam aperture device is perpendicular to the ray beam outlet window such that the side faces of the planer beam-shaping element are oriented approximately parallel to the X-ray beam bundle.

15. The X-ray emitter of claim 14, further comprising:
- a collimator, wherein the extra-focal beam aperture device is between the X-ray tube and the collimator, wherein the collimator is oriented for collimation of the useful X-ray beam.

16. The X-ray emitter of claim 14, wherein the X-ray tube is rotatable relative to the extra-focal beam aperture device.

\* \* \* \* \*